United States Patent [19]

Aung et al.

[11] Patent Number: 5,261,414
[45] Date of Patent: Nov. 16, 1993

[54] BLOOD PRESSURE MONITOR SYSTEM

[75] Inventors: Ye Aung; Masami Takaya, both of Komaki; Hideo Nishibayashi, Inuyama, all of Japan

[73] Assignee: Colin Electronics Co., Ltd., Aichi, Japan

[21] Appl. No.: 901,091

[22] Filed: Jun. 19, 1992

[30] Foreign Application Priority Data

Jun. 28, 1991 [JP] Japan .................. 3-185687

[51] Int. Cl.$^5$ .............................................. A61B 5/02
[52] U.S. Cl. ..................... 128/683; 128/690
[58] Field of Search ................ 128/678–683, 128/687–690, 677, 672

[56] References Cited

U.S. PATENT DOCUMENTS 4,360,029 11/1982 Ramsey, III .
4,427,013 1/1984 Nunn et al. .................. 128/681
4,928,701 5/1990 Harada et al. .
5,101,829 4/1992 Fujikawa et al. .

FOREIGN PATENT DOCUMENTS 0152848 8/1985 European Pat. Off. .
0154995 8/1985 European Pat. Off. .
0297146 1/1989 European Pat. Off. .
WO88/04910 7/1988 PCT Int'l Appl. .
WO89/09017 10/1989 PCT Int'l Appl. .

Primary Examiner—Lee S. Cohen
Assistant Examiner—Marianne Parker
Attorney, Agent, or Firm—Oliff & Berridge

[57] ABSTRACT

A blood pressure monitor system for monitoring blood pressure of a living subject, including a pulse wave detecting device detecting a first pulse wave produced from an artery of the subject via a body surface of the subject over the artery, an inflatable cuff pressing a body portion of the subject, a blood pressure measuring device measuring a systolic and a mean blood pressure of the subject, based on variation in amplitude of pulses of a second pulse wave transmitted to the cuff by changing a pressure in the cuff, and a blood pressure determining device determining a relationship between blood pressure and pulse wave magnitude, based on the systolic and mean blood pressure values measured by the blood pressure measuring device and an upper-peak magnitude and a mean magnitude of the first pulse wave detected by the pulse wave detecting device, and continuously determining, according to the relationship, blood pressure values of the subject based on magnitudes of the first pulse wave detected by the pulse wave detecting device.

10 Claims, 5 Drawing Sheets

BLOOD PRESSURE MONITOR SYSTEM

BACKGROUND OF THE INVENTION

1. Field of the Invention

The present invention relates in general to a blood pressure monitor system and in particular to such a monitor system which continuously determines blood pressure values of a living subject, according to a relationship between blood pressure and pulse wave magnitude, based on detected magnitudes of the pulse wave.

2. Related Art Statement

There is known a blood pressure monitor apparatus of the type which (a) presses a body portion (e.g., upper arm) of a patient by inflating a cuff wound around the upper arm, (b) detects an oscillatory pressure wave transmitted from the upper arm to the cuff in synchronism with heartbeat of the patient, or a start and an end of arterial sounds (i.e., Korotkoff sounds) produced from a brachial artery in the upper arm of the patient, while the air pressure in the inflated cuff is slowly lowered, (c) measures a systolic and a diastolic blood pressure of the subject based on the variation of the oscillatory pressure wave or based on the start and end of the Korotkoff sounds, (d) detects a pressure pulse wave produced from an artery (e.g., radial artery) of the patient by using a semiconductor pressure sensing means, (e) determines a relationship between blood pressure and pulse wave magnitude (hereinafter, abbreviated to the "BP-PW relationship"), based on the systolic and diastolic blood pressure values measured by using the cuff and two pulse wave magnitudes detected by the pressure sensing means, (f) updates the BP-PW relationship at predetermined intervals of time, and (g) continuously determines or estimates, according to the currently effective BP-PW relationship, blood pressure values of the patient based on detected magnitudes of the pressure pulse wave. Thus, this apparatus is capable of monitoring the blood pressure of the patient for a long time, without so frequently pressing the upper arm of the patient by inflating the cuff. This apparatus is disclosed in U.S. Pat. No. 4,928,701 assigned to the Assignee of the present application.

In the above-identified monitor apparatus, the BP-PW relationship is determined by solving the simultaneous equations of first degree with two unknowns in which a measured systolic blood pressure is associated with a detected upper-peak (maximum) magnitude of a pulse of the pressure pulse wave and a measured diastolic blood pressure is associated with a detected lower-peak (minimum) magnitude of the same pulse or another pulse. The BP-PW relationship is expressed by the following linear function: $BP = a \cdot M + b$, in which BP represents blood pressure, M represents pulse wave magnitude, and a and b are constants. Therefore, the accuracy of determination of blood pressure values by this apparatus depends on the accuracy of the BP-PW relationship. It is however known that, generally, diastolic blood pressure values of a subject measured by using an inflatable cuff suffer from considerably large variance. Since the apparatus determines and updates the BP-PW relationship based on diastolic blood pressure values that may be largely variable, the apparatus may not accurately determine or estimate blood pressure values of the subject.

In addition, in the case where the cuff is set upstream of the pulse wave sensing means on the same and one limb of the patient, the pulse wave sensor cannot detect the pressure pulse wave from the radial artery and therefore the apparatus cannot monitor the blood pressure of the patient, during the periods of measurement of systolic and diastolic blood pressure values using the cuff, because the blood flow from the brachial artery to the radial artery is blocked by the inflated cuff.

SUMMARY OF THE INVENTION

It is therefore an object of the present invention to provide a blood pressure monitor system which monitors patient's blood pressure with high accuracy and shortens the periods of interruption of the blood pressure monitoring in the case where both the cuff and the pulse wave sensing means are set on the same and one limb of the patient.

The above object has been achieved by the present invention, which provides a blood pressure monitor system for monitoring blood pressure of a living subject, comprising (a) pulse wave detecting means for detecting a first pulse wave produced from an artery of the subject via a body surface of the subject over the artery, (b) an inflatable cuff for pressing a body portion of the subject, (c) blood pressure measuring means for measuring a systolic and a mean blood pressure of the subject based on variation in amplitude of pulses of a second pulse wave transmitted to the cuff by changing a pressure in the cuff, and a blood pressure determining means for determining a relationship between blood pressure and pulse wave magnitude based on the systolic and mean blood pressure values measured by the blood pressure measuring means and an upper-peak magnitude and a mean magnitude of the first pulse wave detected by the pulse wave detecting means, and continuously determining, according to the relationship, blood pressure values of the subject based on magnitudes of the first pulse wave detected by the pulse wave detecting means.

In the blood pressure monitor system constructed as described above, the blood pressure determining means determines a relationship between blood pressure and pulse wave magnitude, based on the systolic and mean blood pressure values measured by the blood pressure measuring means and the upper-peak and mean magnitudes of the first pulse wave detected by the pulse wave detecting means, and continuously determines, according to the thus determined relationship, blood pressure values of the subject based on magnitudes of the first pulse wave detected by the pulse wave detecting means. Thus, the present monitor system continuously monitors the blood pressure of the subject. Mean blood pressure values measured by using the cuff do not vary, therefore are stable and reliable. Since the reliable means blood pressure values are utilized for determining the BP-PW relationship, the present monitor system provides blood pressure values of high accuracy. In addition, the blood pressure measuring means determines the systolic and mean blood pressure values based on the amplitude variation of respective pulses of the second pulse wave transmitted to the cuff by changing the pressure in the cuff. This blood pressure measurement method is so-called "oscillometric" method. The oscillometric method permits a mean blood pressure to be measured before a diastolic blood pressure is measured. More specifically, when the pressure of the cuff is lowered to a level equal to a mean blood pressure of the subject, the monitor system can terminate the blood pressure measurement, without further lowering the cuff pressure to a level equal to a diastolic blood pressure, therefore, even where the cuff and the pulse wave detecting means are set on the same limb of the subject, the present system shortens the periods of interruption of the continuous blood pressure monitoring due to the blood pressure measurements using the cuff.

According to a preferred feature of the present invention, while the blood pressure measuring means decreases the pressure in the cuff, the blood pressure measuring means calculates a difference between the amplitudes of each pair of time-wise adjacent two pulses out of the respective pulses of the second pulse wave and determines as the systolic blood pressure of the subject a pressure in the cuff when the differences between the amplitudes of the pairs of pulses become maximum, and subsequently determines as the mean blood pressure of the subject a pressure in the cuff when the amplitudes of the respective pulses of the second pulse wave become maximum.

According to another feature of the present invention, the pulse wave detecting means includes at least one pressure sensor each of which detects the first pulse wave transmitted thereto from the artery of the subject via the body surface of the subject, and produces an electric signal indicative of the detected first pulse wave, the detecting means defining a variable line indicative of a magnitude of the electric signal, and determining, as a mean magnitude of one pulse of the first pulse wave, a magnitude of the electric signal indicated by the variable line when a first area bounded by the variable line and an upper portion of the electric signal corresponding to the one pulse which portion is positioned above the variable line, is equal to a second area bounded by the variable line and a lower portion of the electric signal corresponding to the one pulse which portion is positioned beneath the variable line. Alternatively, the detecting means may define a first and a second line each indicative of a magnitude of the electric signal and determine, as a mean magnitude of one pulse of the first pulse wave, a magnitude of the electric signal indicated by the first line which passes bary-centric coordinates of an area bounded by the electric signal corresponding to the one pulse and the second line passing a lower-peak point of the one pulse.

According to yet another feature of the present invention, the blood pressure determining means determines as the relationship the following linear function:

$$y = \alpha \cdot x + \beta$$

in which
x: the pulse wave magnitude,
y: the blood pressure, and
$\alpha, \beta$: constants,
the blood pressure determining means determining the constants $\alpha, \beta$ by solving the following simultaneous equations with the two unknowns $\alpha, \beta$:

$$P_{sys} = \alpha \cdot ST_{max} + \beta$$

$$P_{mean} = \alpha \cdot ST_{mean} + \beta$$

in which
$P_{sys}$: the systolic blood pressure,
$ST_{max}$: the upper-peak magnitude of the first pulse wave,
$P_{mean}$: the mean blood pressure, and
$ST_{mean}$: the mean magnitude of said first pulse wave.

According to a further feature of the present invention, the blood pressure determining means successively calculates a systolic and diastolic blood pressure values of the subject, according to the relationship, based on an upper-peak and a lower-peak magnitude of each of pulses of the first pulse wave detected by the pulse wave detecting means after the relationship is determined.

In another embodiment of the present invention, the blood pressure determining means updates the relationship at predetermined intervals of time, based on pairs of systolic and mean blood pressure values measured by the blood pressure measuring means at the predetermined intervals.

In yet another embodiment of the present invention, the monitor system further comprises display means for successively displaying, along a time axis, the blood pressure values determined by the blood pressure determining means.

In a further embodiment of the present invention, the the pulse wave detecting means comprises a sensor chip including a semiconductor substrate and a plurality of pressure sensing elements formed in one of opposite surfaces of the substrate, and pressing means for pressing the sensor chip against the artery via the body surface so as to partially flatten a wall of the artery, so that each of the pressure sensing elements detects the first pulse wave transmitted to the one surface of the substrate from inside the artery via the flattened wall of the artery and the body surface over the artery.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENTS

Figure 1:
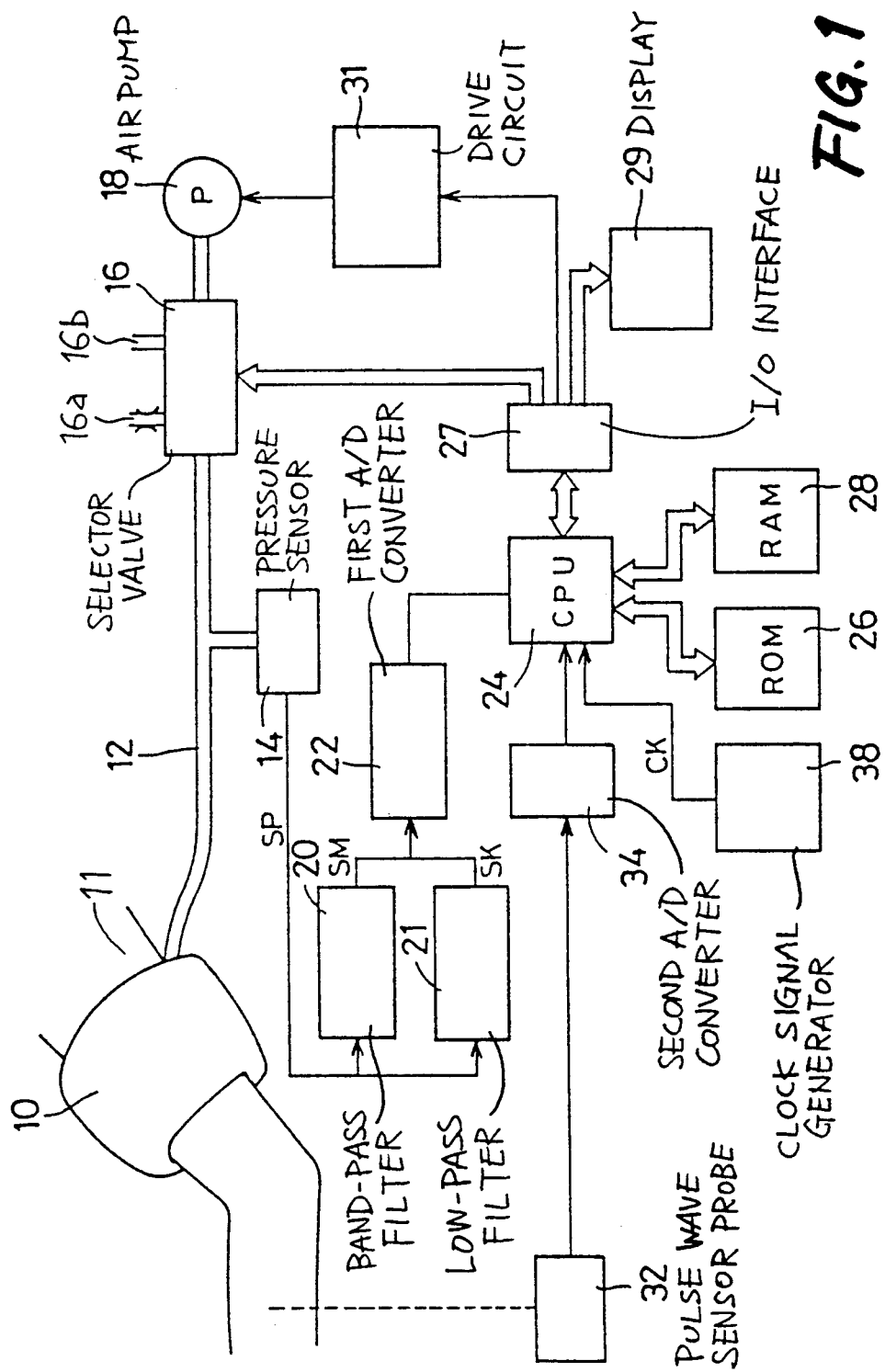
FIG. 1 is a diagrammatic view of a blood pressure monitor system embodying the present invention.

Referring first to FIG. 1, there is shown a blood pressure monitor system embodying the present invention. In the figure, reference numeral 10 designates a bag-like, inflatable cuff formed of rubber. The cuff 10 is worn on a living body such as a patient by being wound around, for example, an upper arm of the patient. A pressure sensor 14, a selector valve 16, and an air pump 18 are connected to the cuff 10 via flexible piping 12.

The pressure sensor 14 detects the air pressure in the cuff 10 (hereinafter, referred to as the "cuff pressure"), and supplies an electric signal, SP, representative of the detected cuff pressure, to a band-pass filter 20 and a low-pass filter 21. The band-pass filter 20 has a specific band of frequencies corresponding to the frequency of an oscillatory component ("Alternating Current (AC)" component) of the pressure signal SP produced in synchronism with heartbeat of the patient, and transmits only the oscillatory signal component. Hereinafter, the oscillatory signal component is referred to as the "cuff pulse wave signal SM". The cuff pulse wave signal SM is representative of the oscillatory pressure wave (i.e., pulse wave) transmitted from the upper arm to the cuff 10 in synchronism with the heartbeat of the patient, when the cuff pressure is slowly lowered. Thus, the band-pass filter 20 separates the cuff pulse wave signal SM from the pressure signal SP and supplies the signal SM to a central processing unit (CPU) 24 via a first analog to digital (A/D) converter 22.

The low-pass filter 21 is a high-frequency cutting filter that cuts off high-frequency components from the pressure signal SP. Stated differently, the low-pass filter 21 transmits only a static-pressure signal component ("Direct Current (DC)" component) of the pressure signal SP. Hereinafter, the static-pressure signal component is referred to as the "cuff pressure signal SK". The cuff pressure signal SK is representative of a static pressure, P, of the cuff 10 (hereinafter, referred to as the "cuff static pressure P"). The cuff pressure signal SK is supplied to the CPU 24 via the first A/D converter 26.

Meanwhile, the selector valve 16 is selectively placed in an INFLATION position, a SLOW-DEFLATION position, and a QUICK-DEFLATION position. In the INFLATION position, a slow- and a quick-deflation outlet 16a, 16b of the selector valve 16 both are closed so that pressurized air is supplied from the air pump 18 to the cuff 10 until the cuff static pressure P is increased to a predetermined target pressure level; then, in the SLOW-DEFLATION position, the slow-deflation outlet 16a of the valve 16 is opened so that the pressurized air is slowly discharged from the cuff 10 to the atmosphere at a predetermined rate suitable for blood pressure measurement; and, immediately after the blood pressure measurement terminates during the slow-deflation of the cuff 10, the quick-deflation outlet 16b of the selector valve 16 is opened and thereby the selector valve 16 is placed in the QUICK-DEFLATION position, so that the pressurized air is quickly discharged from the cuff 10 to the atmosphere through the opened outlet 16b.

The CPU 24 is connected via data bus to a read only memory (ROM) 26, a random access memory (RAM) 28, and an input and output (I/0) interface 27. The CPU 24 processes supplied signals according to control programs pre-stored in the ROM by utilizing the temporary-storage function of the RAM. The CPU 24 supplies an ON/OFF signal to a drive circuit 31 connected to the air pump 18 and thereby regulates the supply of electric power to the air pump 18. Thus, the CPU 24 controls the start and stop of the operation of the air pump 18. In addition, the CPU 24 supplies a switch signal to switch the positions of the selector valve 16 and thereby regulates the cuff static pressure P as described above.

Furthermore, the CPU 24 carries out a series of steps for blood pressure measurement according to the control program pre-stored in the ROM 26, and determines a systolic blood pressure value, $P_{sys}$, and a mean blood pressure value, $P_{mean}$, of the patient, based on the cuff pulse wave signal SM and the cuff pressure signal SK. The CPU 24 commands a display 29 to display the measured blood pressure values $P_{sys}$, $P_{mean}$. This control program is described in JIS (Japanese Industrial Standard) T 1115, and a well-known algorithm used as the "oscillometric" blood pressure measurement method. While the cuff static pressure P is slowly decreased from a predetermined pressure level sufficiently higher than an estimated systolic blood pressure of the patient, the CPU 24 reads in the cuff pulse wave signal SM and the cuff static pressure signal SK. The CPU 24 determines as a systolic blood pressure $P_{sys}$ a cuff static pressure P at the time when the amplitudes of respective pulses of the signal SM significantly largely varies, for example, when the rate of change of the amplitudes becomes maximum, and determines as a mean blood pressure $P_{mean}$ a cuff static pressure P at the time when the amplitudes of respective pulses of the signal SM become maximum.

Figure 2:
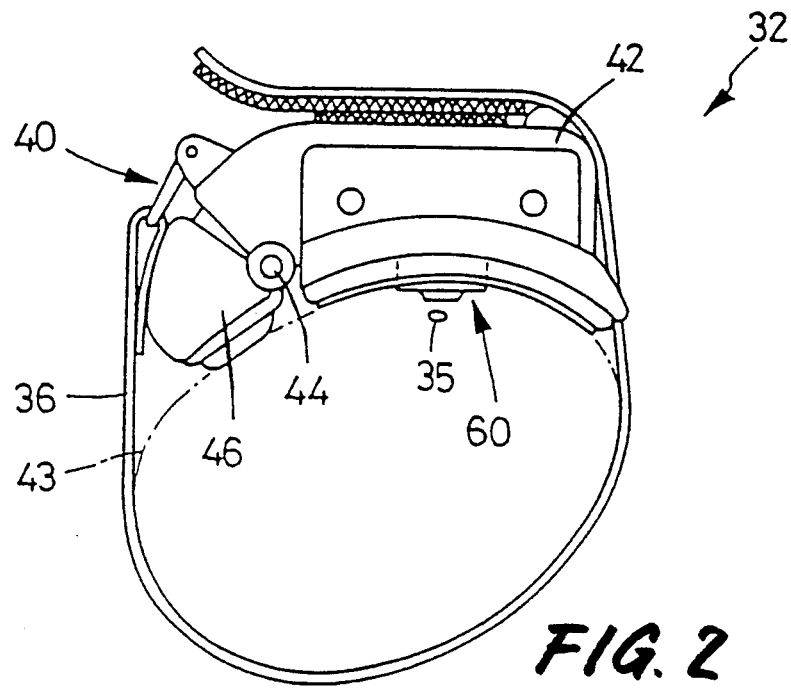
FIG. 2 is a side view of a pulse wave sensor probe of the monitor system of FIG. 1.
Figure 3:
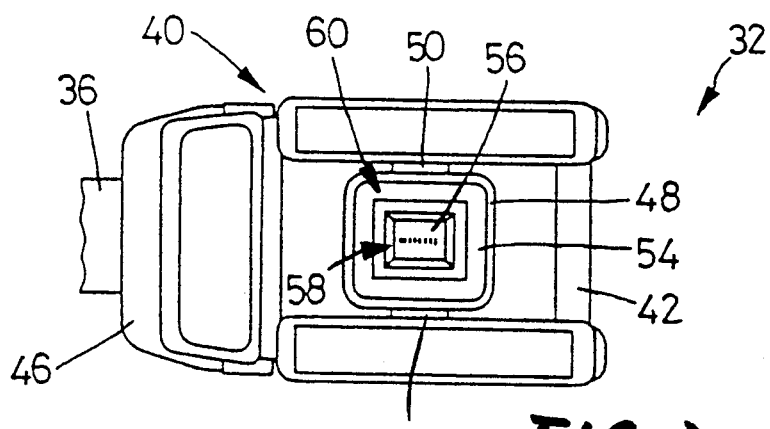
FIG. 3 is a plan view of the pulse wave sensor probe of FIG. 2.

As shown in FIG. 1, the present monitor system further includes a pulse wave sensor probe 32 which is worn on an arm of the patient. The sensor probe 32 serves as pulse wave detecting means. As shown in FIGS. 2 and 3, the sensor probe 32 is detachably set on a wrist of the patient with a pair of bands 36, 36 fastened around the wrist. The bands 36, 36 are provided with a pair of fasteners, respectively. A radial artery 35 located above a radius bone in the wrist is easy to detect pressure pulse wave therefrom. The sensor probe 32 detects the pressure pulse wave from the radial artery, and supplies a pressure pulse wave signal, ST, representing the detected pressure pulse wave, to the CPU 24 via a second A/D converter 34.

A clock signal generator 38 supplies a clock signal, CK, to the CPU 24 at a predetermined frequency.

As shown in FIGS. 2 and 3, the sensor probe 32 includes a housing 40 consisting of a first and a second housing 42, 46 which are pivotally connected to each other by a pin 44. The housing 40 as a whole has a container-like configuration. The first housing 42 has an open end which is adapted to contact a body surface or skin 43 of the wrist. A container-like casing 48 is accommodated in the first housing 42. The casing 48 has an open end which is opposed to the skin 43 when the sensor probe 32 is set on the skin 43. The casing 48 has a pair of opposite arms 50, 52 which respectively engage a pair of guide grooves (not shown) formed with the first housing 42. The casing 48 is also engaged with a feed screw (not show) extending along the longitudinal side of the housing 40, i.e., in a direction generally perpendicular to the direction of extension of the radial artery 35. Thus, when the feed screw is rotated by being driven by an electric motor (not shown) accommodated in the second housing 46, the casing 48 is movable in the direction generally perpendicular to the radial artery 35, as seen in FIG. 2. The first housing 42 also accommodates a reduction gear unit (not shown) which is on one hand operatively connected to one of opposite axial ends of the feed screw located on the side of the second housing 46 and which is on the other hand operatively connected to an output shaft of the above-indicated electric motor via a flexible coupling (not shown). This arrangement ensures that the driving force of the electric motor is transmitted to the feed screw via the reduction gear unit irrespective of the relative angular position between the first and second housings 42, 46.

An elastic diaphragm 54 is supported by an inner wall of the casing 48, so that the diaphragm 54 and the casing 48 cooperate with each other to define a pressure chamber (not shown) on the side of a bottom wall of the casing 48. To an external surface of the diaphragm 54 away from the pressure chamber, a semiconductor pressure sensor chip 60 is secured. The sensor chip 60 has, in a press surface 56 thereof, an array of pressure sensing elements 58 arranged in the direction of movement of the casing 48. When pressurized air is supplied to the pressure chamber and the chamber pressure is raised to about 10 to 100 mmHg, the sensor chip 60 is advanced out of the casing 48 and first housing 42, so that the sensor chip 60 is pressed against the radial artery 35 in such a manner that the wall of the artery 35 is partially flattened.

Figure 4:
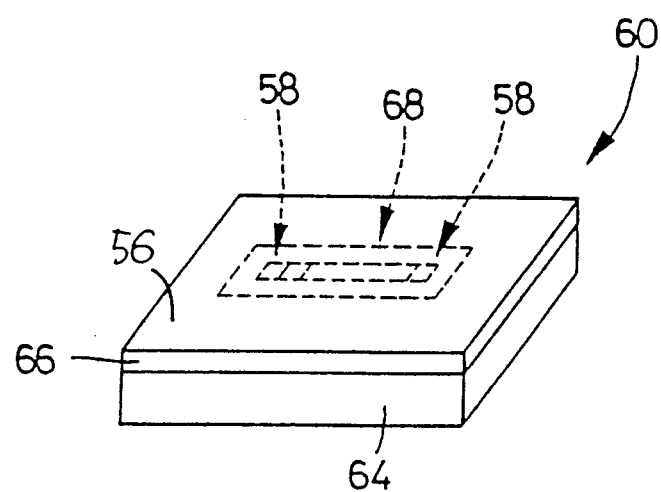
FIG. 4 is a perspective view of a semiconductor pulse wave sensor chip employed in the sensor probe of FIG. 2.

FIG. 4 shows the pressure sensor chip 60. The sensor chip 60 consists of a back-up plate 64 formed of a rigid material such as glass and a semiconductor substrate 66 such as a monocrystalline silicon plate. The semiconductor substrate 66 is adhered to one surface of the back-up plate 64. The semiconductor substrate 66 has a thickness of about 300 microns, and has an elongate recess (not shown) formed in one of opposite surfaces on the side of the back-up plate 64. Thus, the semiconductor substrate 66 includes a diaphragm portion 68 having a reduced thickness of about several to ten and several microns. An array of pressure sensing elements 58 are formed in the diaphragm portion 68 at predetermined intervals of distance (e.g., about 200 microns) along the longitudinal direction of the sensor chip 60. Each pressure sensing element 58 is constituted by a resistance bridge consisting of four resistance elements provided by a well-known semiconductor production process such as impurity diffusion or injection. Additional description of this sensor chip 60 is provided in U.S. Pat. No. 5,101,829 assigned to the Assignee of the present application. Each pressure sensing element 58 detects strain or pressure variation (i.e., pressure pulse wave) applied to the press surface 56 (or diaphragm portion 68) of the sensor ship 60 and provides as a pulse wave signal ST an electric signal indicative of the detected pressure variation.

The sensor chip 60 is pressed against the radial artery 35 via the skin 43 in such a manner that the array of pressure sensing elements 58 are located above the artery 35 and extends in the direction generally perpendicular to the artery 35. With the artery 35 partially flattened under the pressing force of the sensor chip 60, each pressure sensing element 58 produces a pulse wave signal ST indicative of the pressure pulse wave transmitted from inside the artery 35 to the press surface 56 via the flattened wall of the artery 35 and the skin 43 located between the flattened wall of the artery 35 and the press surface 56.

Before the pulse wave sensor probe 32 detects the pressure pulse wave from the radial artery 35, a control device (not shown) operates, based on the pressure pulse wave signals ST from the individual pressure sensing elements 58, for actuating the above-mentioned electric motor to displace the casing 48 to an optimum position on the skin 43 where the pressure sensing elements 58 are positioned above the radial artery 35. In addition, by utilizing the signals ST supplied from the elements 58 in the process of increasing the pressure in the pressure chamber in the casing 48, the control device determines an optimum pressure to be applied to the pressure chamber of the casing 48, that is, optimum pressing force to be applied to the sensor chip 60 to press the artery 35 to partially flatten the wall of the artery 35. This technique is known in the art. With the sensor chip 60 being held at the optimum position and pressed with the optimum pressing force, an optimum one of the pressure sensing elements 58 which is located directly above the artery 35 can detect a pressure pulse wave which is free of the tensile or elastic force produced in the wall of the artery 35 and generates a pulse wave signal ST accurately representing the blood pressure inside the artery 35. The technique of selecting the above-mentioned optimum element 58 is also known in the art.

Figure 5:
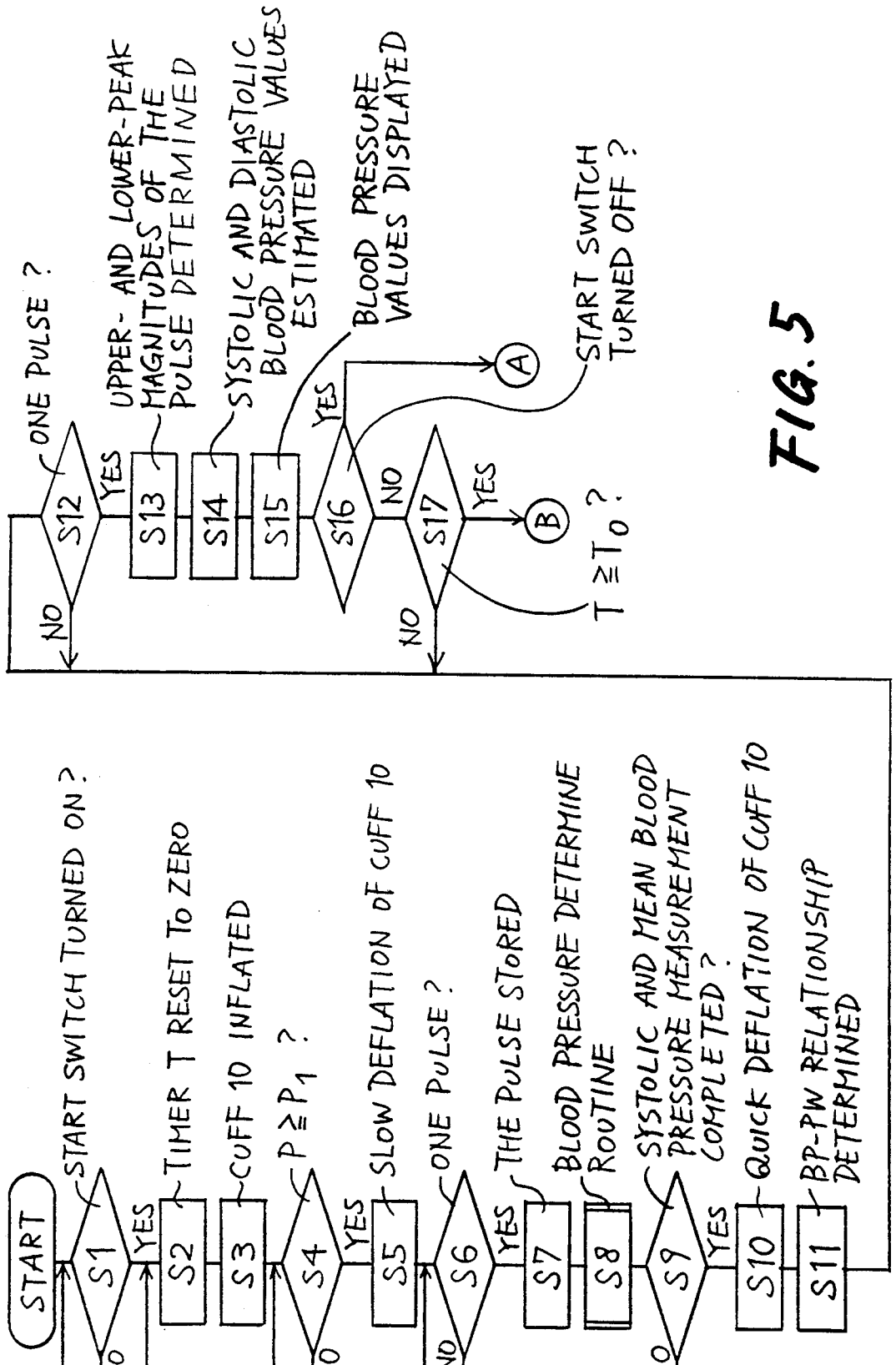
FIG. 5 is a flow chart representing the blood pressure monitor operation of the monitor system of FIG. 1.

Hereinafter, there will be described the operation of the blood pressure monitor system constructed as described above, by reference to the flow chart of FIG. 5.

First, upon application of electric power to the present system, an initialization step (not shown) is carried out. Subsequently, the control of the CPU 24 proceeds with Step S1 to judge whether or not a START switch not shown) has been turned ON, that is, whether or not a monitor-start signal is supplied to, and present at, the CPU 24. Usually, the START switch is turned ON after the cuff 10 is wound around the upper arm of a patient and the pulse wave sensor probe 32 is worn on the wrist of the arm of the patient. When the START switch is operated and the monitor-start signal is present at the CPU 24, the control of the CPU 24 goes to Step S2 to clear the contents of a timer T provided in the RAM 28, that is, reset the timer T to zero. The timer T measures time by counting and registering the number of clock signals CK supplied from the clock signal generator 38. The contents of the timer T are used by the CPU 24 for judging whether or not to calibrate the monitor system. After being reset to zero, the timer T starts counting the clock signals CK supplied thereto.

Step S2 is followed by Step S3 to switch the selector valve 16 to the INFLATION position and actuates the air pump 18 to supply pressurized air to the cuff 10. Thus, the cuff static pressure P, represented by the cuff static pressure signal SK, is increased. Step S3 is followed by Step S4 to judge whether or not the cuff static pressure P has exceeded a predetermined target pressure level $P_1$. The target pressure level $P_1$ is pre-determined to be higher (e.g., about 180 mmHg) than an estimated systolic blood pressure of the patient. When the cuff 10 is increased up to the target level $P_1$, the control of the CPU 24 goes to Step S5 to stop the air pump 18 and switch the selector valve 16 from the INFLATION position to the SLOW-DEFLATION position. Thus, the cuff 10 is deflated at a low rate of 2 to 3 mmHg/sec. During this slow deflation of the cuff 10, Step S6 is carried out to judge, based on the cuff pulse wave signal SM, whether or not one pulse of the cuff pulse wave signal SM corresponding to one heartbeat of the patient has been supplied from the band-pass filter 20. If a negative judgement (NO) is made in Step S6, the CPU 24 waits, that is, repeats Step S6. Meanwhile, if an affirmative judgement (YES) is made in Step S6, the control of the CPU 24 goes to Step S7 to determine an amplitude of that one pulse by subtracting a lower-peak magnitude of the pulse from an upper-peak magnitude of the same pulse, and store the determined amplitude together with a cuff static pressure P at the time of occurrence of that one pulse.

Subsequently, the control of the CPU 24 goes to Step S8 to carry out the blood pressure determine routine in which a systolic and a mean blood pressure are determined based on variation of the amplitudes of the respective pulses of the cuff pulse wave signal SM which has been supplied to the CPU 24 up to the current time during the cuff slow-deflation process. Specifically, the CPU 24 determines, as an actual or standard systolic blood pressure $P_{sys}$, a cuff static pressure P at the time when the amplitudes of the respective pulses significantly largely change, that is, when the differences between pairs of time-wise adjacent two amplitudes of respective pulses of the cuff pulse wave signal SM become maximum. This time corresponds to the time when the rate of change of the amplitudes of the pulses becomes maximum. Subsequently, the CPU 24 determines, as an actual or standard mean blood pressure $P_{mean}$, a cuff static pressure P at the time when the amplitudes of the respective pulses become maximum, that is, at the time of occurrence of one of the pulses which has a maximum amplitude of all the amplitudes of other pulses. The thus determined systolic and mean blood pressure values $P_{sys}$, $P_{mean}$ are stored in the RAM 28.

Step S8 is followed by Step S9 to judge whether or not the systolic and mean blood pressure values $P_{sys}$, $P_{mean}$ have been determined in Step S8. When a negative judgement is made in Step S8, the CPU 24 repeats Steps S6 to S8.

Meanwhile, if an affirmative judgement is made in Step S9, the control of the CPU 24 goes to Step S10 to switch the selector valve 16 from the SLOW-DEFLATION position to the QUICK-DEFLATION position, thereby causing the cuff 10 to quickly be deflated. Then, in Step S11, the CPU 24 determines a relationship between blood pressure and pulse wave magnitude (BP-PW relationship), based on the systolic and mean blood pressure values $P_{sys}$, $P_{mean}$ determined in Step S8 and the pressure pulse wave signal ST supplied from the optimum pressure sensing element 58 located directly above the radial artery 35. Specifically, the CPU 24 determines an upper-peak (maximum) magnitude, $ST_{max}$, of a pulse of the signal ST which pulse is detected at the time when the rate of change of the amplitudes of the pulses of the signal SM becomes maximum, that is, when the cuff static pressure P is equal to the systolic blood pressure value $P_{sys}$, and a mean magnitude, $ST_{mean}$, of a pulse of the signal ST which pulse is detected at the time when the amplitudes of the pulses of the signal ST become maximum, that is, when the cuff static pressure P is equal to the mean blood pressure value $P_{mean}$.

Figure 6:
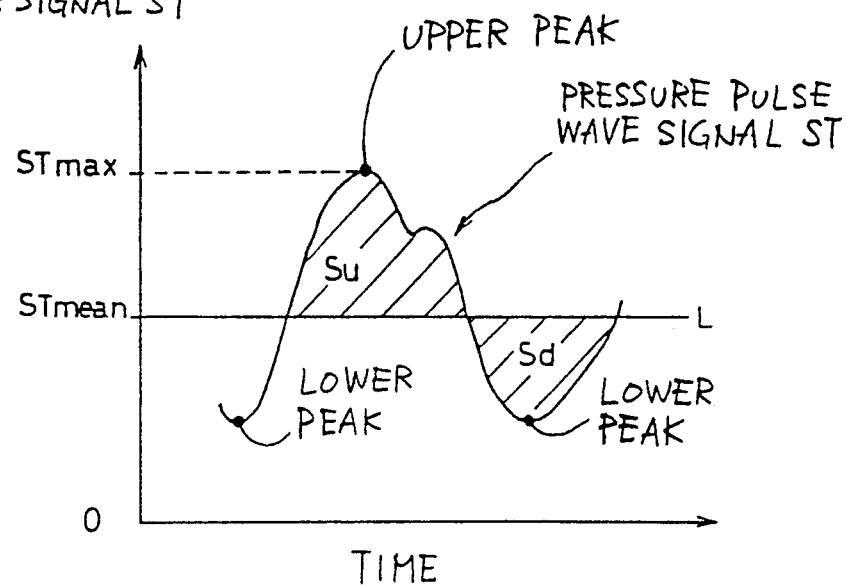
FIG. 6 is a graph for illustrating the manner of determining a mean magnitude, $ST_{mean}$, of a pulse of the pulse wave in Step S11 of the flow chart of FIG. 5.

FIG. 6 shows the manner of determining a mean magnitude $ST_{mean}$ of a pulse of the pressure pulse wave signal ST. The CPU 24 determines as the mean pulse magnitude $ST_{mean}$ a signal magnitude indicated by a line, L, when an area, Su, bounded by the line L and an upper portion of the one-pulse signal ST above the line L is equal to an area, Sd, bounded by the line L and a lower portion of the one-pulse signal ST beneath the line L.

For example, the BP-PW relationship is expressed by the following linear function:

$$y = \alpha \cdot x + \beta \tag{1}$$

in which
x: pulse wave magnitude;
y: estimated blood pressure value; and
$\alpha, \beta$: constants.

The constants $\alpha$, $\beta$ are determined by solving the following simultaneous equations of first order with the two unknowns $\alpha$, $\beta$:

$$P_{sys} = \alpha \cdot ST_{max} + \beta$$

$$P_{mean} = \alpha \cdot ST_{mean} + \beta$$

The BP-PW relationship may be approximated by a quadratic or higher-order function which satisfies the two pairs of coordinates $(T_{max}, P_{sys})$ and $(T_{mean}, P_{mean})$.

Furthermore, the CPU 24 may be adapted to determine as the mean magnitude $ST_{mean}$ a signal magnitude indicated by a line passing the bary-centric coordinates of an area bounded by the one-pulse signal ST and a line passing a lower-peak point of the one pulse.

Figure 7:
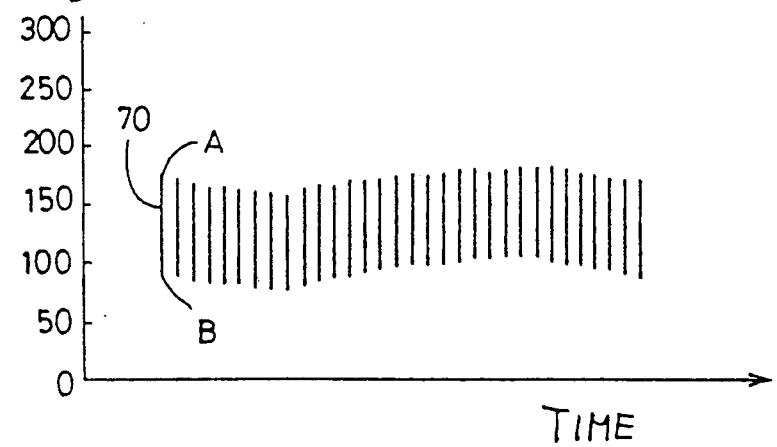
FIG. 7 is a graph for illustrating a time-wise varying trend of the blood pressure of a subject displayed on a display device of the monitor system of FIG. 1 as a result of carrying out the flow chart of FIG. 5.

After the BP-PW relationship has been determined in Step S11, the control of the CPU 24 goes to Step S12 to whether or not one pulse of the pressure pulse wave signal ST has been supplied from the optimum pressure sensing element 58 directly above the radial artery 35. If an affirmative judgement is made in Step S12, the control goes to Step S13 to determine the upper-peak and lower-peak magnitudes, $ST_{max}$ and $ST_{min}$, of that pulse. Step S13 is followed by Step S14 to estimate a systolic and a diastolic blood pressure, $P_{sys(es)}$ and $P_{dia(es)}$, according to the BP-PW relationship expressed by the above-indicated linear function (1), based on the upper-peak and lower-peak magnitudes $ST_{max}$ and $ST_{min}$ determined in Step S13. Specifically, each of the values $P_{sys(es)}$ and $P_{dia(es)}$ is calculated as the variable y by replacing the variable x with a corresponding one of the values $ST_{max}$ and $ST_{min}$. Subsequently, the control of the CPU 24 goes to Step S15 to supply a display signal to the display 29 so as to indicate, on a cathode ray tube (CRT) thereof, the thus determined systolic and diastolic blood pressure values $P_{sys(es)}$ and $P_{dia(es)}$. FIG. 7 shows a time-wise varying trend of the blood pressure of the patient, indicated in the graph provided on the display 29. In the figure, the top and bottom ends, A and B, of each bar 70 correspond to the systolic and diastolic blood pressure values of the patient. The display 29 continuously or successively displays the bars 70 each of which corresponds to one heartbeat of the patient.

Step S15 is followed by Step S16 to judge whether or not the START switch has been turned OFF to stop the operation of the present monitor system, that is, whether or not a monitor-stop signal is present at the CPU 24. If an affirmative judgement is made in Step S16, the control of the CPU 24 goes back to Step S1. On the other hand, if a negative judgement is made in Step S16, the control goes to Step S17 to judge whether or not the contents of the timer T have exceeded a reference value, $T_o$, indicative of a pre-determined interval of time employed for periodically calibrating the monitor system, that is, updating the BP-PW relationship. For example, the reference time $T_o$ is pre-determined at 10 to 20 minutes.

Short after the initiation of the monitoring operation, a negative judgement is made in Step S17, and the CPU 24 repeats Steps S12 to S17. Consequently, the display 29 continues to display successive bars 70 each indicative of estimated blood pressure values of the patient. Meanwhile, when the contents of the timer T are increased up to the reference value $T_o$ and accordingly an affirmative judgement is made in Step S17, the control of the CPU 24 goes back to Step S2 and the following steps. In short, in Step S8, another pair of standard systolic and mean blood pressure values $P_{sys}$, $P_{mean}$ are determined and, in Step S11, another BP-PW relationship is determined based on the thus determined values $P_{sys}$, $P_{mean}$ and an upper-peak and a mean magnitude of the signal ST detected when the cuff static pressure P is equal to the systolic or mean blood pressure $P_{sys}$, $P_{mean}$, respectively. The BP-PW relationship is updated by replacing the previous one with the newly determined one. According to the updated BP-PW relationship, the CPU 24 continuously estimates systolic and diastolic blood pressure values $P_{sys(es)}$, $P_{dia(es)}$ of the patient based on the upper-peak and lower-peak magnitudes $ST_{max}$, $ST_{min}$ of each of respective pulses of the pressure pulse wave signal ST read in after the BP-PW relationship is updated. The pairs of values $P_{sys(es)}$, $P_{dia(es)}$ are successively displayed as respective bars 70 on the display 29.

In the present embodiment, the pressure sensor 14, air pump 18, filters 20, 21, Step S8, a portion of the CPU 24, ROM 26 and RAM 28 for carrying out Step S8, and others cooperate with each other to serve as blood pressure measuring means for measuring actual or standard systolic and mean blood pressure values of a living subject by varying the cuff static pressure P; the pulse wave sensor probe 32 serves as pulse wave detecting means; and Steps S11 to S14 and a portion of the CPU 24, ROM 26 and RAM 28 for carrying out Steps S11 to S14 cooperate with each other to serve as blood pressure determining means for determining a BP-PW relationship based on the systolic and mean blood pressure values $P_{sys}$, $P_{mean}$ measured by the blood pressure measuring means and an upper-peak magnitude and a mean magnitude of the pressure pulse wave signal ST supplied from the pulse wave detecting means, and continuously determining, according to the BP-PW relationship, blood pressure values of the subject based on magnitudes of the pressure pulse wave actually detected by the pulse wave detecting means. Thus, the present monitor system monitors the blood pressure of a patient for a long period of time, for example, during or after a surgical operation of the patient.

As is apparent from the foregoing, in the present monitor system, the BP-PW relationship is determined and updated by utilizing mean blood pressure values $P_{mean}$ that are more reliable than diastolic blood pressure values $P_{dia}$ involving a considerably large variance. Thus, the BP-PW relationship is very reliable and accurate, which ensures that accurate blood pressure values $P_{sys(es)}$, $P_{dia(es)}$ are determined.

In addition, in Step S8, the CPU 24 can terminate the blood pressure measurement immediately after the cuff static pressure P is lowered down to a mean blood pressure $P_{mean}$ of the patient, since the systolic and mean blood pressure measurement is carried out by the oscillometric method. Thus, the present monitor system reduces the time required for carrying out the blood pressure measurement, in comparison with the measurement time for the case where diastolic blood pressure values are used for determining and updating the BP-PW relationship. Therefore, in the case where the pulse wave sensor probe 32 is set on the same limb of the patient as that on which the cuff 10 is set, the monitor system advantageously shortens each period of interruption of the blood pressure monitoring due to the blocking of the blood flow under the cuff 10 inflated for measurement of the actual blood pressure values.

While the present invention has been described in its presently preferred embodiment, it is to be understood that the invention may otherwise be embodied.

Although in the illustrated embodiment the pulse wave sensor probe 32 is adapted to detect the pressure pulse wave from the radial artery 35 in the wrist of a subject, it is possible to adapt the sensor probe 32 to detect the pressure pulse wave from other arteries, such as a carotid artery and a pedal dosal artery, located near the body surface of the subject from which the pressure pulse wave is easily detected.

While in the illustrated embodiment the pulse wave sensor chip 60 including a plurality of pressure sensing elements 58 is used, it is possible to employ for the detection of pressure pulse wave a pressure sensor having a single point or location of detection. Alternatively, the pressure pulse wave detecting means may be constituted by a small-volume flexible rubber bag which is used by being wound around a limb of a subject and held at a constant pressure, and a pressure sensor provided inside the rubber bag to detect as the pressure pulse wave the pressure variation inside the rubber bag.

It is to be understood that the present invention may be embodied with other changes, modifications, and improvements that may occur to those skilled in the art without departing from the scope and spirit of the invention defined in the appended claims.

What is claimed is:

1. A blood pressure monitor system for monitoring blood pressure of a living subject, comprising:

pulse wave detecting means for detecting a series of pulses of a first pulse wave produced from an artery of said subject via a body surface of the subject over said artery;

an inflatable cuff for pressing a body portion of said subject;

blood pressure measuring means for measuring a systolic and a mean blood pressure of said subject based on variation in amplitude of a series of pulses of a second pulse wave which is produced from the pressed body portion of said subject and is propagated to said inflatable cuff by changing a pressure in said cuff; and blood pressure determining means for determining a relationship between blood pressure and pulse wave magnitude, based on the systolic and mean blood pressure values measured by said blood pressure measuring means and an upper-peak magnitude and a mean magnitude of at least one of said pulses of said first pulse wave detected by said pulse wave detecting means, and continuously determining, according to said relationship, blood pressure values of said subject based on magnitudes of said first pulse wave detected by said pulse wave detecting means.

2. The blood pressure monitory system as set forth in claim 1, wherein, while said blood pressure measuring means decreases the pressure in said cuff, said blood pressure measuring means calculates a difference between the amplitudes of each pair of time-wise adjacent two pulses of said pulses of said second pulse wave and determines as said systolic blood pressure of said subject a pressure in said cuff when the differences between the amplitudes of the pairs of pulses become maximum, and subsequently determines as said mean blood pressure a pressure in said cuff when the amplitudes of said pulses of said second pulse wave become maximum.

3. The blood pressure monitor system as set forth in claim 1, wherein said pulse wave detecting means includes at least one pressure sensor which detects said series of pulses of said first pulse wave transmitted thereto from said artery of said subject via said body surface of the subject, and produces an electric signal which is indicative of the detected pulses of said first pulse wave along a time axis, said pulse wave detecting means defining a variable line which extends parallel to said time axis and is indicative of a magnitude of said electric signal, and superimposing said variable line on one of said detected pulses of said first pulse wave, said pulse wave detecting means specifying, by moving said variable line over said one pulse in a direction perpendicular to said time axis, a magnitude of said variable line at a time when a first area bounded by said variable line and an upper portion of an electric signal indicative of said one pulse which upper portion is of a magnitude greater than said variable line, becomes equal to a second area bounded by said variable line and a lower portion of the electric signal indicative of said one pulse which lower portion is of a magnitude less than said variable line, said pulse wave detecting means determining the specified magnitude of said variable line as a mean magnitude of said one pulse of said first pulse wave.

4. The blood pressure monitor system as set forth in claim 1, wherein said pulse wave detecting means includes at least one pressure sensor which detects said series of pulses of said first pulse wave transmitted thereto from said artery of said subject via said body surface of the subject, and produces an electric signal which is indicative of the detected pulses of said first pulse wave along a time axis, said pulse wave detecting means establishing a coordinate system defined by said time axis and a signal magnitude axis representative of magnitude of said electric signal, and defining a first and a second line which extend parallel to said time axis and are indicative of a first and a second magnitude of said electric signal, respectively, and superimposing said first and second lines on one of said detected pulses of said first pulse wave such that said second line passes through a lower-peak point of said one pulse and said first line passes through bary-center coordinates of an area bounded by said second line and the electric signal indicative of said one pulse, said pulse wave detecting means determining said first magnitude of said first variable line as a mean magnitude of said one pulse of said first pulse wave.

5. The blood pressure monitor system as set forth in claim 1, wherein said blood pressure determining means determines as said relationship the following linear function:

$$y = a \cdot x + \beta$$

in which
x: said pulse wave magnitude,
y: said blood pressure, and
$a, \beta$: constants, said blood pressure determining means determining said constants $a, \beta$ by solving the following simultaneous equations with the two unknowns $a, \beta$:

$$P_{sys} = a \cdot ST_{max} + \beta$$

$$P_{mean} = a \cdot ST_{mean} + \beta$$

in which
$P_{sys}$: said systolic blood pressure;
$ST_{max}$: said upper-peak magnitude of said first pulse wave,
$P_{mean}$: said mean blood pressure, and
$ST_{mean}$: said mean magnitude of said first pulse wave.

6. The blood pressure monitor system as set forth in claim 1, wherein said pulse wave detecting means detects an upper-peak and a lower-peak magnitude of each of said series of pulses of said first pulse wave, and said blood pressure determining means successively calculates a systolic and a diastolic blood pressure value of said subject, according to said relationship, based on said upper-peak and lower-peak magnitudes, respectively, of said each pulse of said first pulse wave detected by said pulse wave detecting means after said relationship is determined.

7. The blood pressure monitor system as set forth in claim 1, wherein said blood pressure determining means updates said relationship at predetermined intervals of time, based on pairs of systolic and mean blood pressure values measured by said blood pressure measuring means at said predetermined intervals.

8. The blood pressure monitor system as set forth in claim 1, further comprising display means for successively displaying, along a time axis, said blood pressure values determined by said blood pressure determining means.

9. The blood pressure monitor system as set forth in claim 1, wherein said pulse wave detecting means comprises:

a sensor chip including a semiconductor substrate and a plurality of pressure sensing elements formed in one of opposite surfaces of said substrate; and pressing means for pressing said sensor chip against said artery via said body surface so as to partially flatten a wall of the artery, so that each of said pressure sensing elements detects said first pulse wave transmitted to said one surface of said substrate from inside said artery via the flattened wall of the artery and said body surface over the artery.

10. The blood pressure monitor system as set forth in claim 1, wherein said blood pressure measuring means comprises cuff pressure detecting means for detecting said pressure in said cuff when the cuff pressure is changed, said cuff pressure detecting means including a pressure sensor, and piping for communicating said cuff with said pressure sensor.

* * * * *